(12) United States Patent
Ma et al.

(10) Patent No.: US 11,319,353 B2
(45) Date of Patent: May 3, 2022

(54) **RECOMBINANT *DERMATOPHAGOIDES PTERONYSSINUS* TYPE 2 ALLERGEN PROTEIN AND ITS PREPARATION METHOD AND APPLICATION**

(71) Applicant: ZONHON BIOPHARMA INSTITUTE, INC, Jiangsu (CN)

(72) Inventors: Bruce Yong Ma, Jiangsu (CN); Yu Fan, Jiangsu (CN); Anliang Wang, Jiangsu (CN); Jun Wang, Jiangsu (CN)

(73) Assignee: ZONHON BIOPHARMA INSTITUTE, INC

( * ) Notice: Subject to any disclaimer, the term of this patent is extended or adjusted under 35 U.S.C. 154(b) by 371 days.

(21) Appl. No.: 16/474,217

(22) PCT Filed: Dec. 28, 2017

(86) PCT No.: PCT/CN2017/119173
§ 371 (c)(1),
(2) Date: Jun. 27, 2019

(87) PCT Pub. No.: WO2018/121633
PCT Pub. Date: Jul. 5, 2018

(65) Prior Publication Data
US 2020/0131235 A1 Apr. 30, 2020

(30) Foreign Application Priority Data
Dec. 31, 2016 (CN) .......................... 201611267033.8

(51) Int. Cl.
| C07K 14/435 | (2006.01) |
| A61P 37/08 | (2006.01) |
| A61K 39/35 | (2006.01) |
| C12N 15/81 | (2006.01) |

(52) U.S. Cl.
CPC ........ *C07K 14/43531* (2013.01); *A61K 39/35* (2013.01); *A61P 37/08* (2018.01); *C12N 15/815* (2013.01)

(58) Field of Classification Search
None
See application file for complete search history.

(56) References Cited

U.S. PATENT DOCUMENTS 5,968,526 A * 10/1999 Garman ........... C07K 14/43531
424/275.1
2011/0293665 A1 12/2011 Bordas et al.

FOREIGN PATENT DOCUMENTS

| CN | 1385528 A | 12/2002 | | |
| CN | 102732541 A | 10/2012 | | |
| CN | 105307679 A | 2/2016 | | |
| WO | WO 1999/34826 | * | 7/1999 | ............. A61K 39/35 |
| WO | WO 2003/047618 | * | 6/2003 | ............. A61K 39/35 |

OTHER PUBLICATIONS

Cui, Y.-B., "Registration No. EU346693.1, *Dermatophagoides pteronyssinus* Der p 2 allergen mRNA, complete cds" GenBank Database, Jan. 7, 2008 (Jan. 7, 2008), see nucleotide.
International Search Report and Written Opinion in International Application No. PCT/CN2017/119173 dated Apr. 3, 2018.

* cited by examiner

*Primary Examiner* — Nora M Rooney
(74) *Attorney, Agent, or Firm* — Dilworth IP, LLC

(57) ABSTRACT

A DNA sequence encoding Der p2 protein having a particular base sequence is codon-optimized for the *Pichia pastoris* expression system, which is conducive to expressing Der p2 in *Pichia pastoris*. After gene optimization and adding an activating element to increase the expression of Der p2 in molecular level, it was found that Der p2 is expressed at a higher level as compared with the prior art and has biological activity similar to the natural protein.

Figure 11:
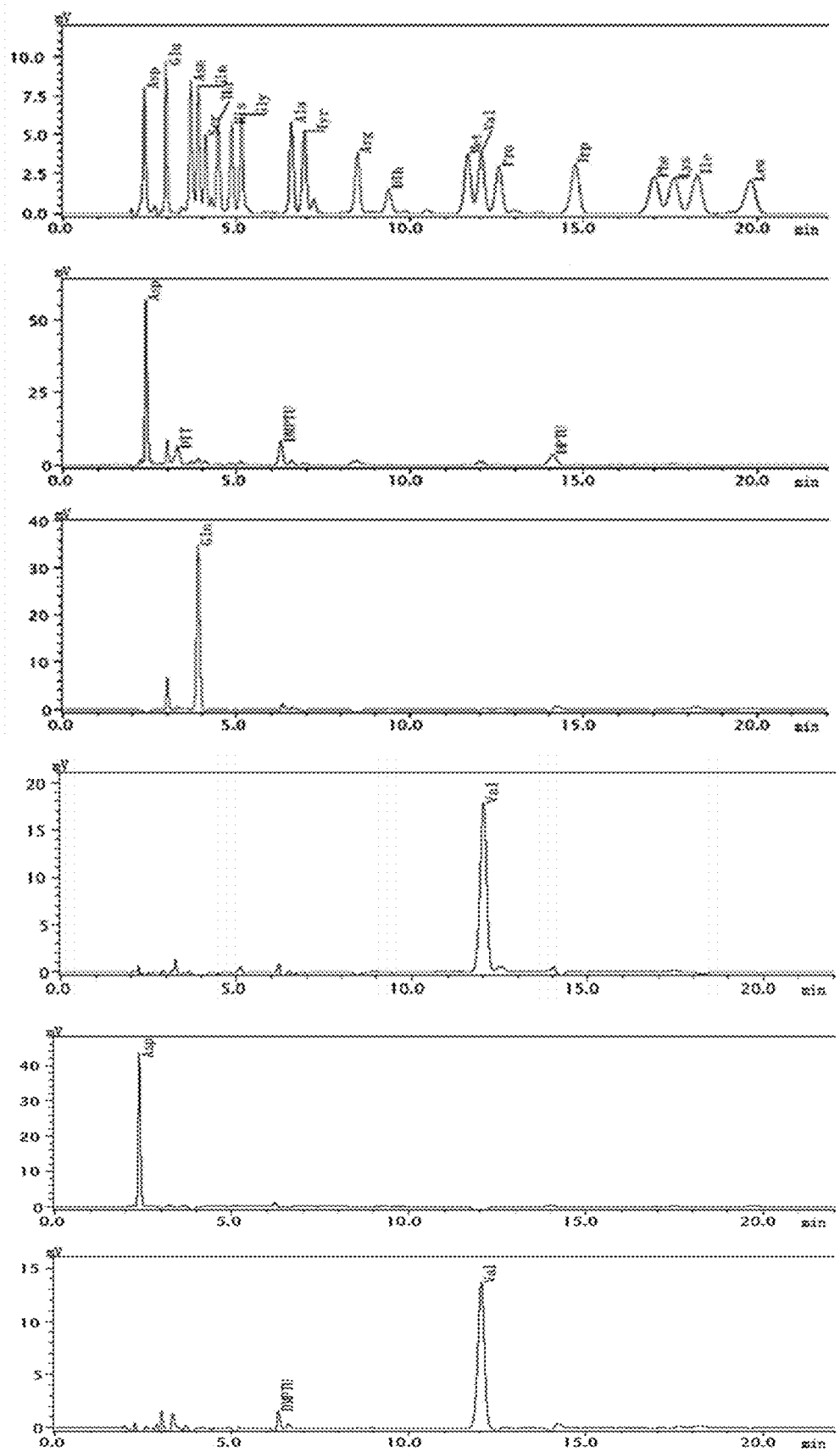

4 Claims, 14 Drawing Sheets
Specification includes a Sequence Listing.

| | | |
|---|---|---|
| Sequence before optimization | 1 | ATGATGTACAAAATTTTGTGTCTTTCATTGTTGGTCGCAGCCGTTGCTCGTGATCAAGTC |
| | | ‖‖‖‖‖‖‖‖‖ ‖‖ ‖‖‖‖‖‖ ‖ ‖‖ ‖‖‖‖‖‖‖ ‖‖ ‖‖ ‖‖‖‖‖ ‖ ‖‖ ‖‖ ‖‖ |
| Sequence after optimization | 1 | ATGATGTACAAGATCTTGTGTTTGTCTTTGTTGGTTGCTGCTGTTGCTAGAGACCAGGTT |
| | 61 | GATGTCAAAGATTGTGCCAATCATGAAATCAAAAAAGTTTTGGTACCAGGATGCCATGGT |
| | | ‖‖ ‖‖ ‖‖ ‖‖ ‖‖‖‖‖ ‖‖ ‖‖ ‖‖ ‖‖‖‖ ‖‖ ‖‖‖‖‖‖‖ ‖‖‖‖‖ ‖‖ ‖‖ ‖‖‖ |
| | 61 | GACGTTAAGGACTGTGCTAACCACGAGATCAAGAAGGTTTTGGTTCCAGGTTGTCACGGT |
| | 121 | TCAGAACCATGTATCATTCATCGTGGTAAACCATTCCAATTGGAAGCCGTTTTCGAAGCC |
| | | ‖‖ ‖‖ ‖‖‖‖‖‖‖‖ ‖‖‖‖‖ ‖ ‖‖‖‖‖ ‖‖‖‖‖‖‖‖ ‖‖‖‖‖ ‖‖ ‖‖‖‖‖‖‖‖‖‖ |
| | 121 | TCCGAGCCATGTATTATTCACAGAGGTAAGCCATTCCAGTTGGAGGCTGTTTTCGAAGCT |
| | 181 | AACCAAAACACAAAAACGGCTAAAATTGAAATCAAAGCCTCAATCGATGGTTTAGAAGTT |
| | | ‖‖‖‖‖ ‖‖‖‖‖ ‖‖ ‖‖ ‖‖‖‖‖ ‖‖‖‖‖ ‖‖‖‖‖ ‖‖ ‖‖ ‖‖‖‖‖ ‖‖‖‖‖ ‖‖‖‖‖‖ |
| | 181 | AACCAGAACACTAAGACTGCTAAGATTGAGATCAAGGCTTCCATCGACGGTTTGGAAGTT |
| | 241 | GATGTTCCCGGTATCGATCCAAATGCATGCCATTACATGAAATGCCCATTGGTTAAAGGA |
| | | ‖‖ ‖‖‖‖‖ ‖‖‖‖‖ ‖‖ ‖‖‖‖‖ ‖‖ ‖‖ ‖‖ ‖‖‖‖‖‖‖‖ ‖‖ ‖‖‖‖‖‖‖‖‖‖‖ ‖‖ |
| | 241 | GACGTTCCAGGTATTGACCCAAACGCTTGTCACTACATGAAGTGTCCATTGGTTAAGGGT |
| | 301 | CAACAATATGATATTAAATATACATGGAATGTTCCGAAAATTGCACCAAAATCTGAAAAT |
| | | ‖‖ ‖‖ ‖‖ ‖‖ ‖‖ ‖‖ ‖‖ ‖‖ ‖‖‖‖‖‖‖‖‖‖‖ ‖‖ ‖‖ ‖‖ ‖‖‖‖‖ ‖‖ ‖‖ ‖‖ |
| | 301 | CAGCAGTACGACATCAAGTACACTTGGAATGTTCCAAAGATCGCTCCAAAGTCCGAGAAC |
| | 361 | GTTGTCGTCACTGTTAAAGTTATGGGTGATGATGGTGTTTTGGCCTGTGCTATTGCTACT |
| | | ‖‖‖‖‖ ‖‖ ‖‖‖‖‖‖‖‖‖ ‖‖‖‖‖‖‖‖‖‖‖ ‖‖ ‖‖‖‖‖‖‖‖‖‖‖ ‖‖‖‖‖‖‖‖‖‖‖‖‖ |
| | 361 | GTTGTTGTTACTGTTAAGGTTATGGGTGACGACGGTGTTTTGGCTTGTGCTATTGCTACT |
| | 421 | CATGCTAAAATCCGCGATTAA |
| | | ‖‖ ‖‖‖‖‖ ‖‖‖ ‖ ‖‖ ‖‖‖ |
| | 421 | CACGCTAAGATCAGAGACTAA |

Figure 1

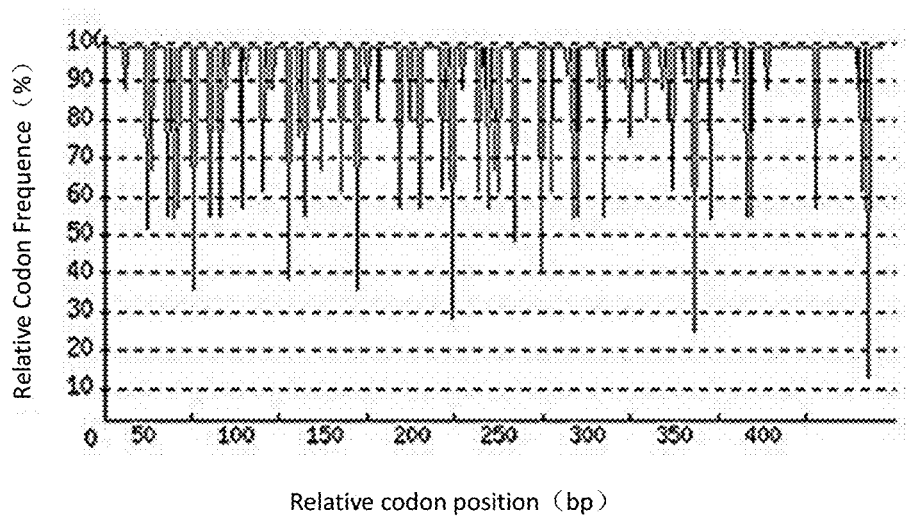

Figure 2-a

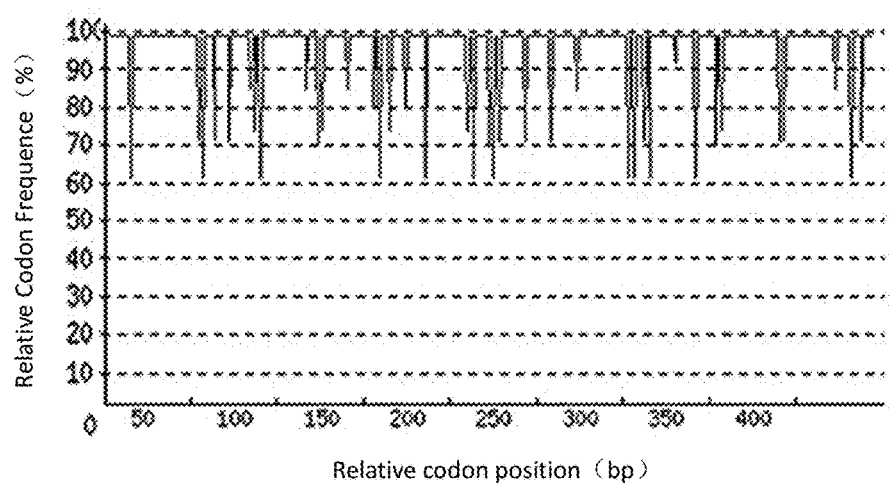
Figure 2-b
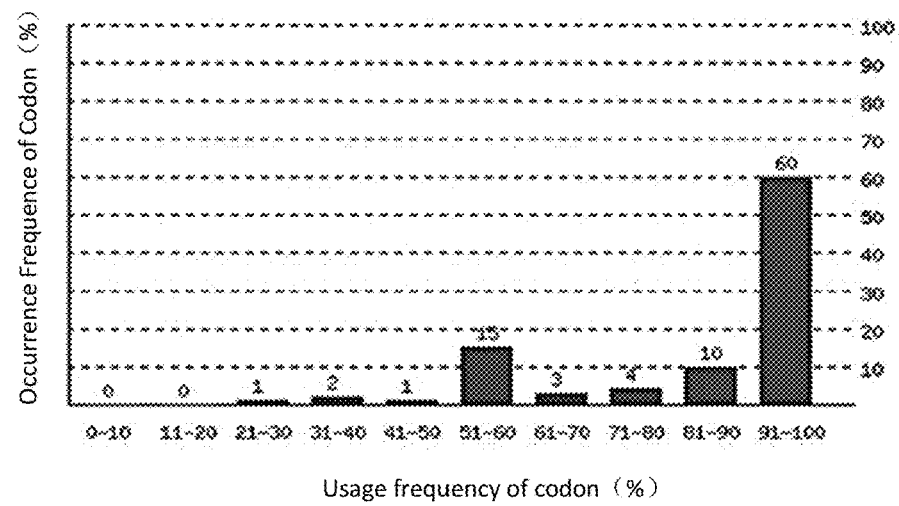
Figure 3-a
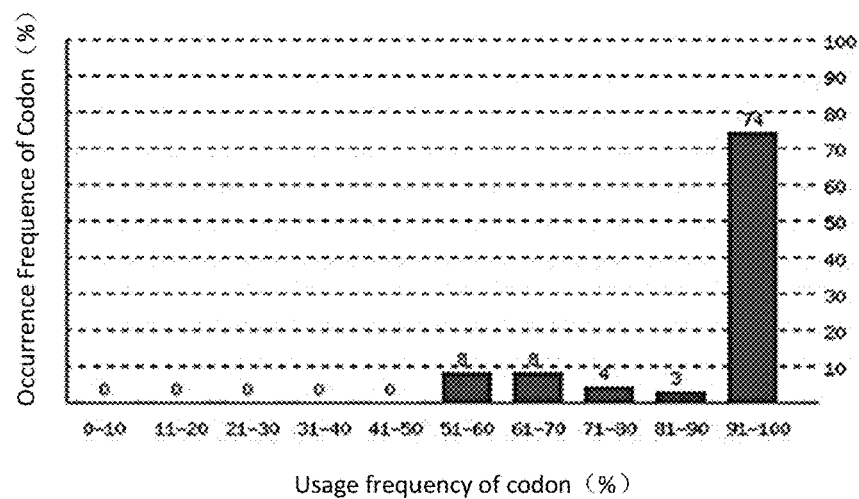
Figure 3-b

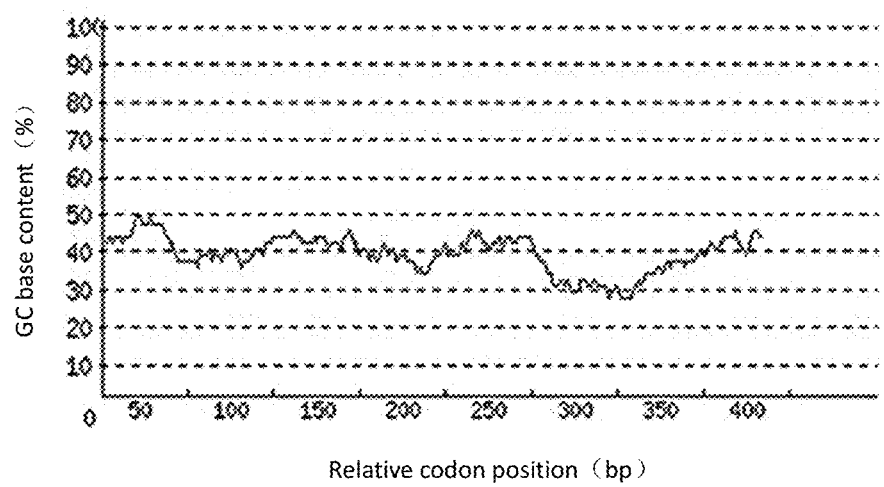
Figure 4-a
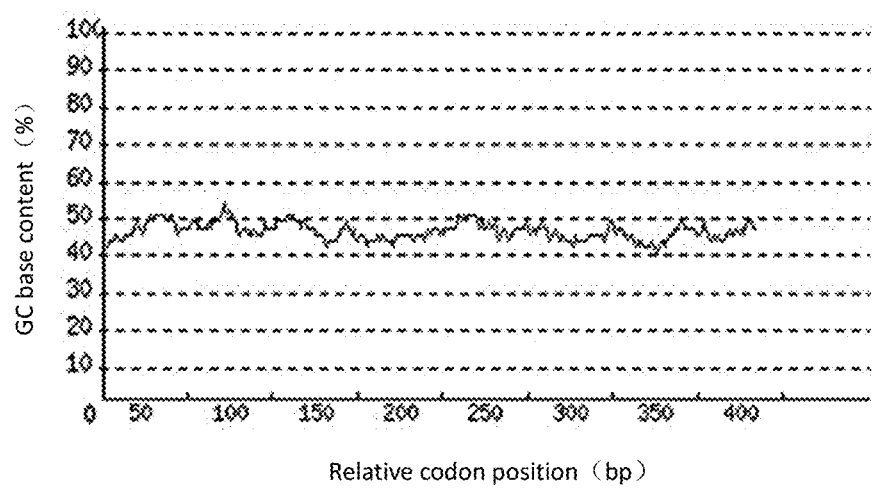
Figure 4-b
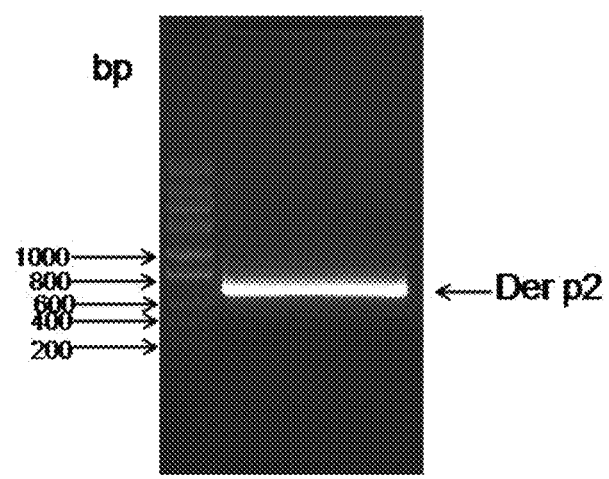
Figure 5

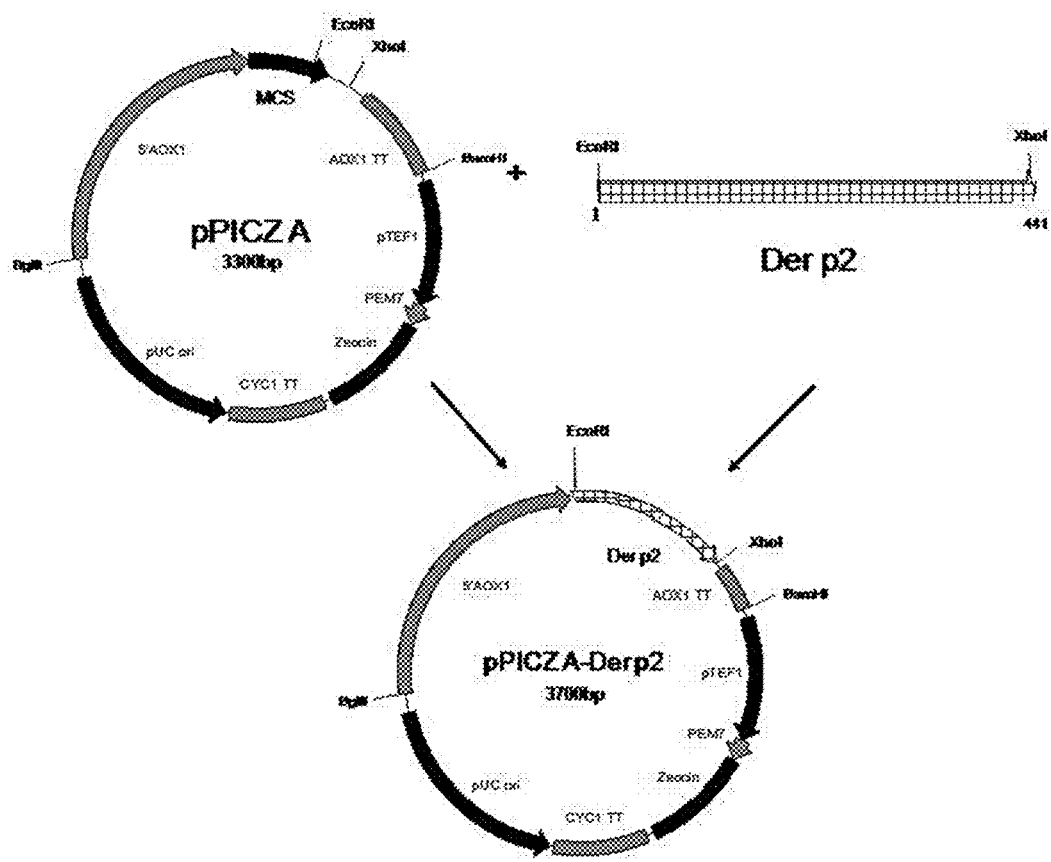
Figure 6
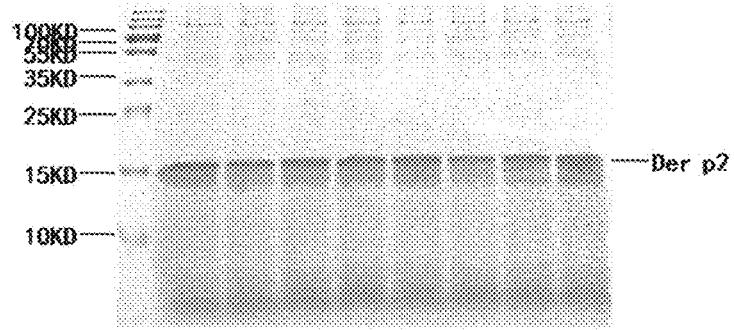
Figure 7-a
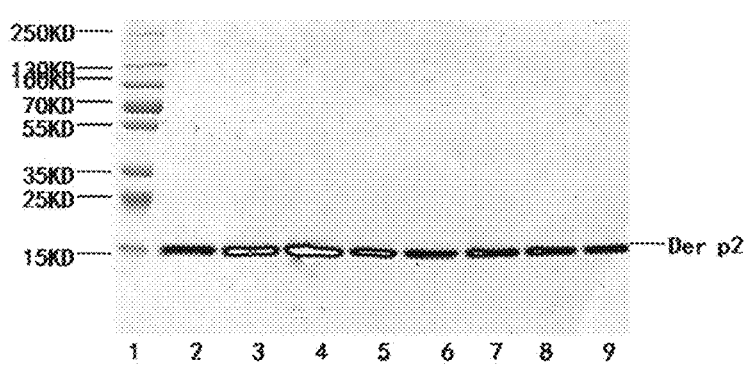
Figure 7-b

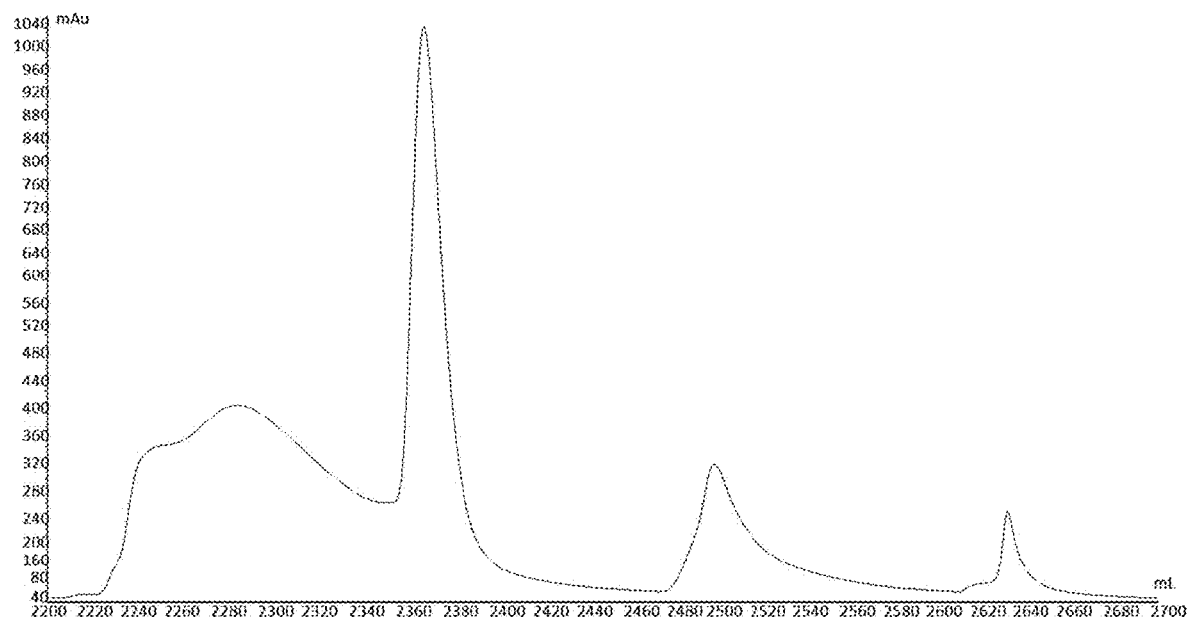
Figure 8-a
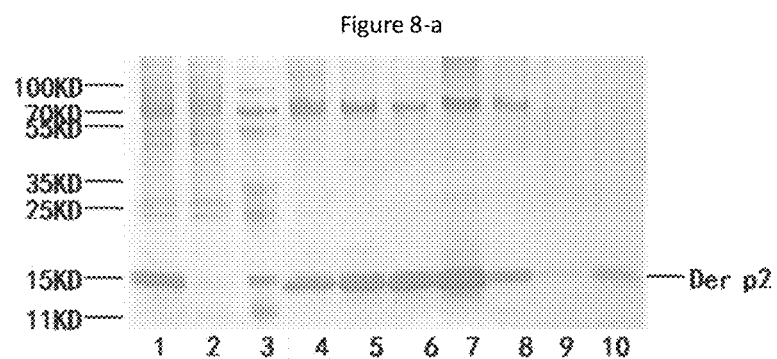
Figure 8-b
Figure 9-a

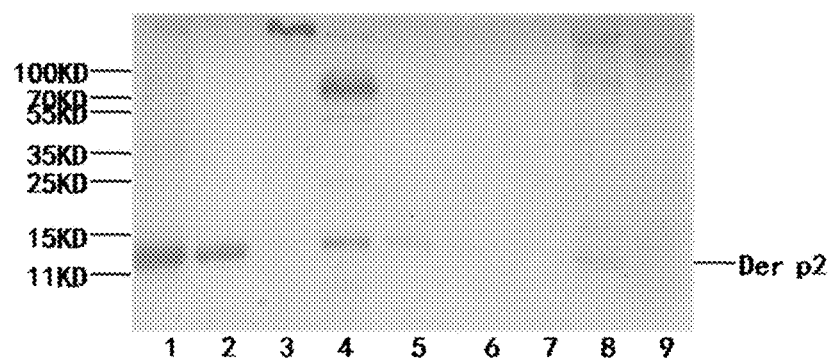
Figure 9-b
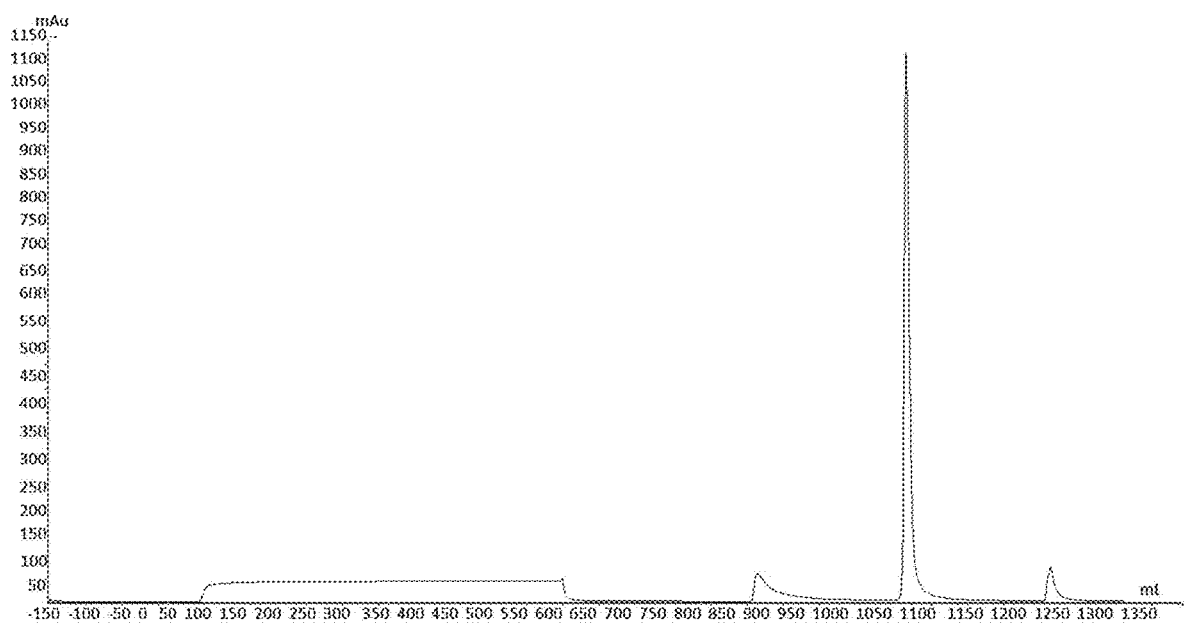
Figure 10-a
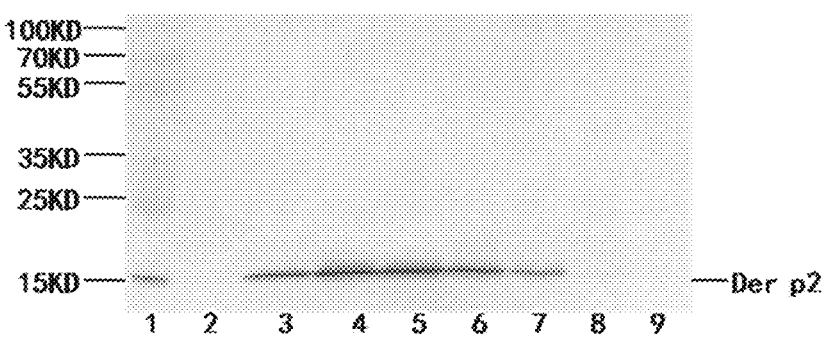
Figure 10-b

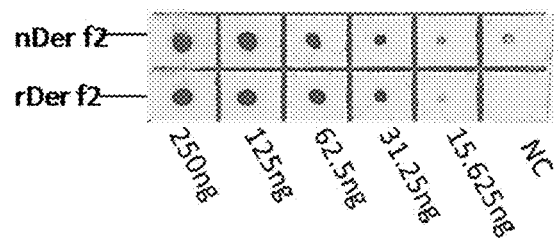
Figure 12
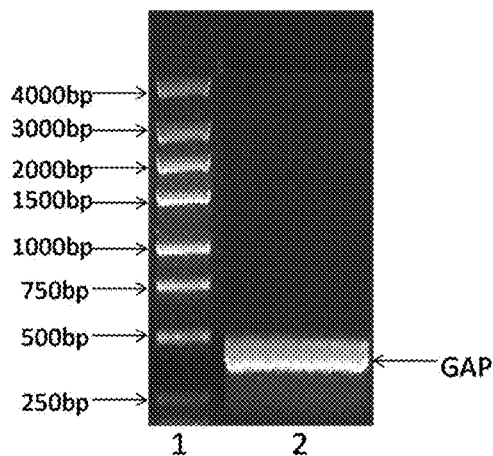
Figure 13
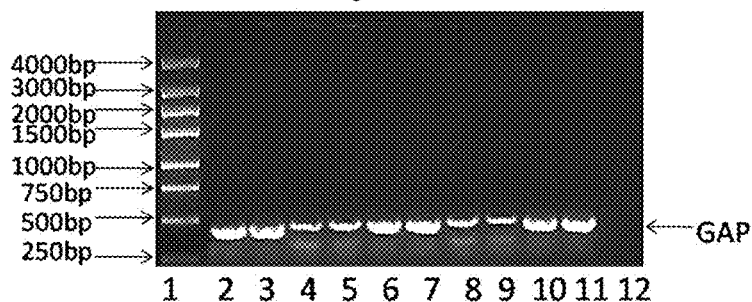
Figure 14
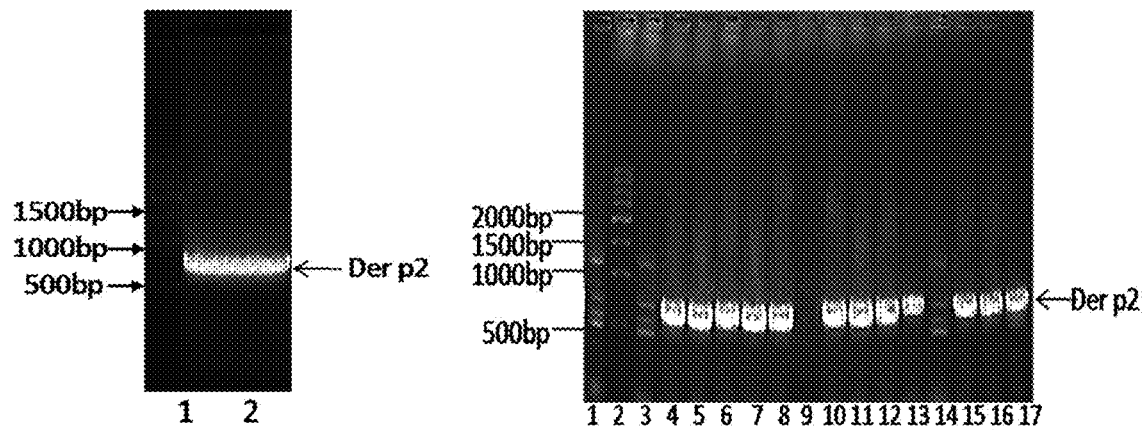
Figure 15
Figure 16

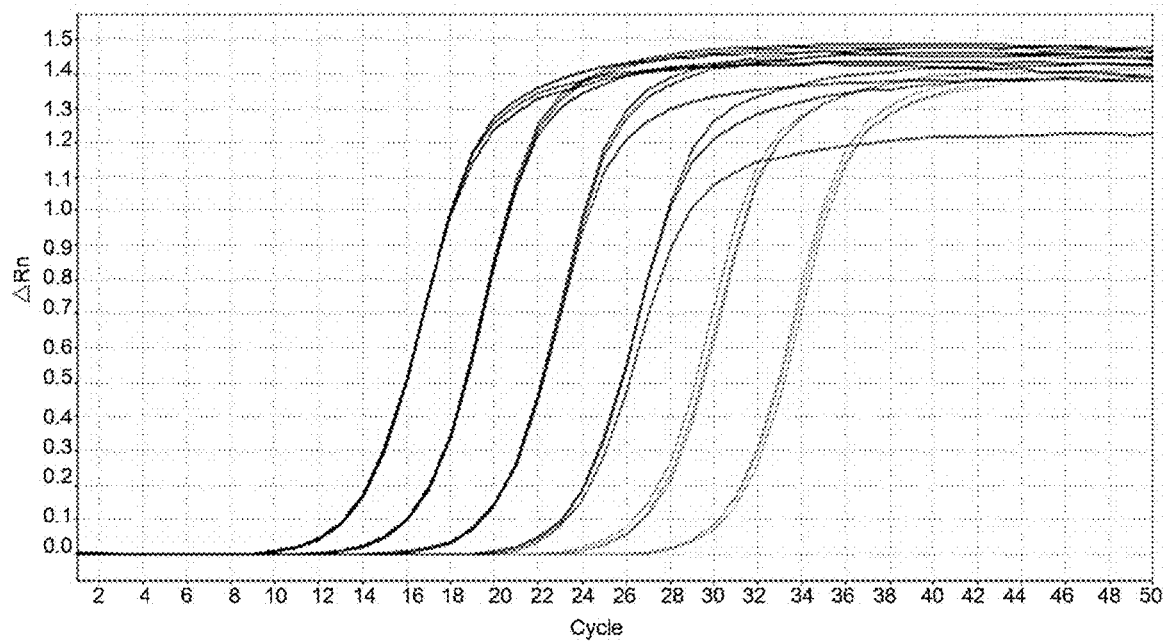
Figure 17-a
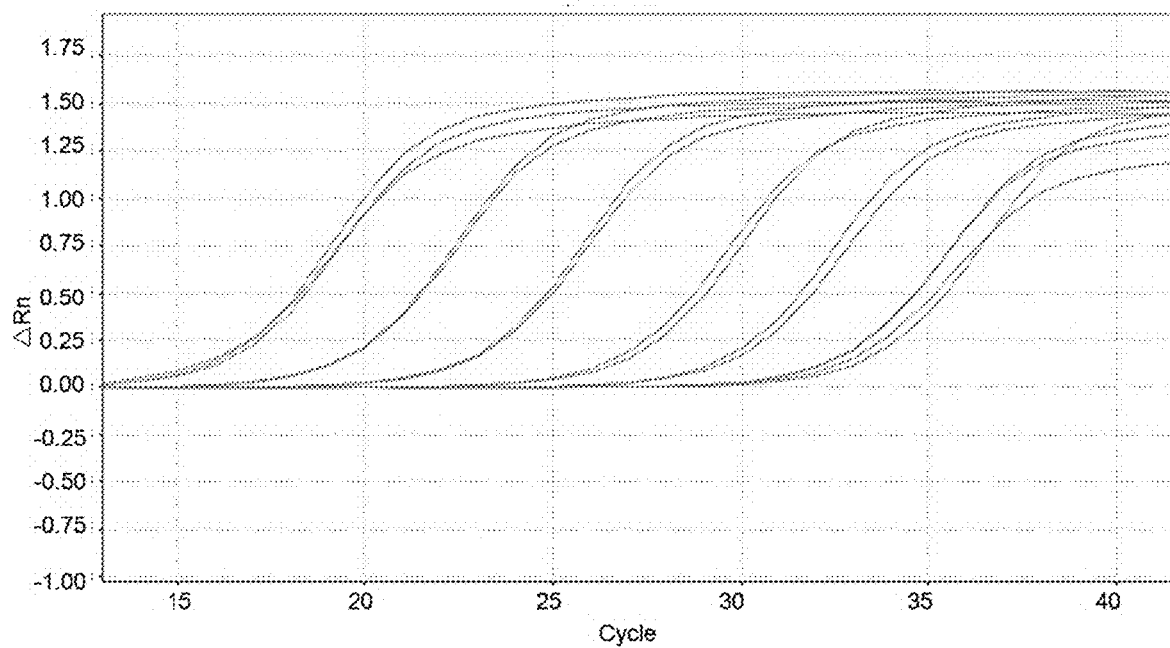
Figure 17-b

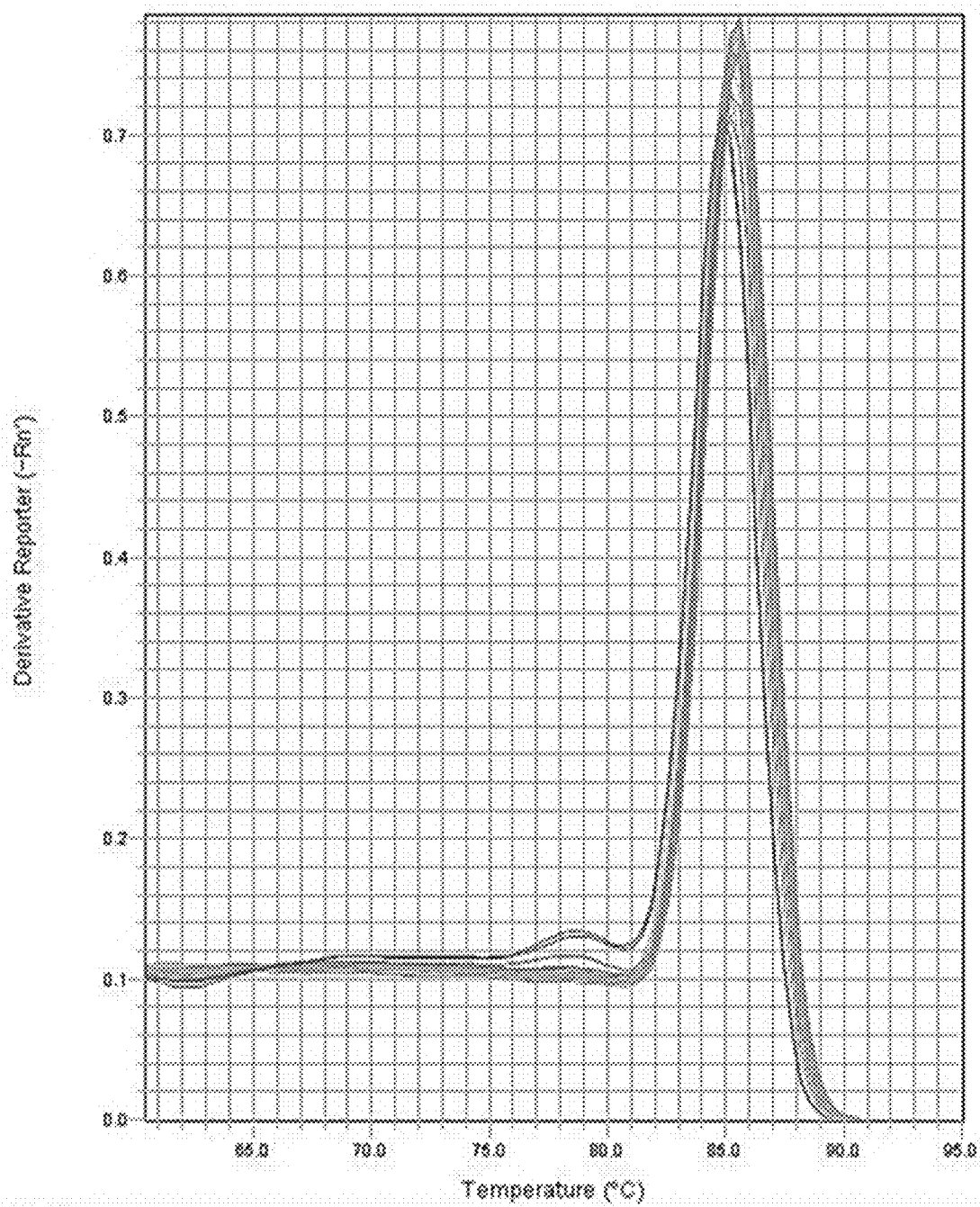
Figure 18-a

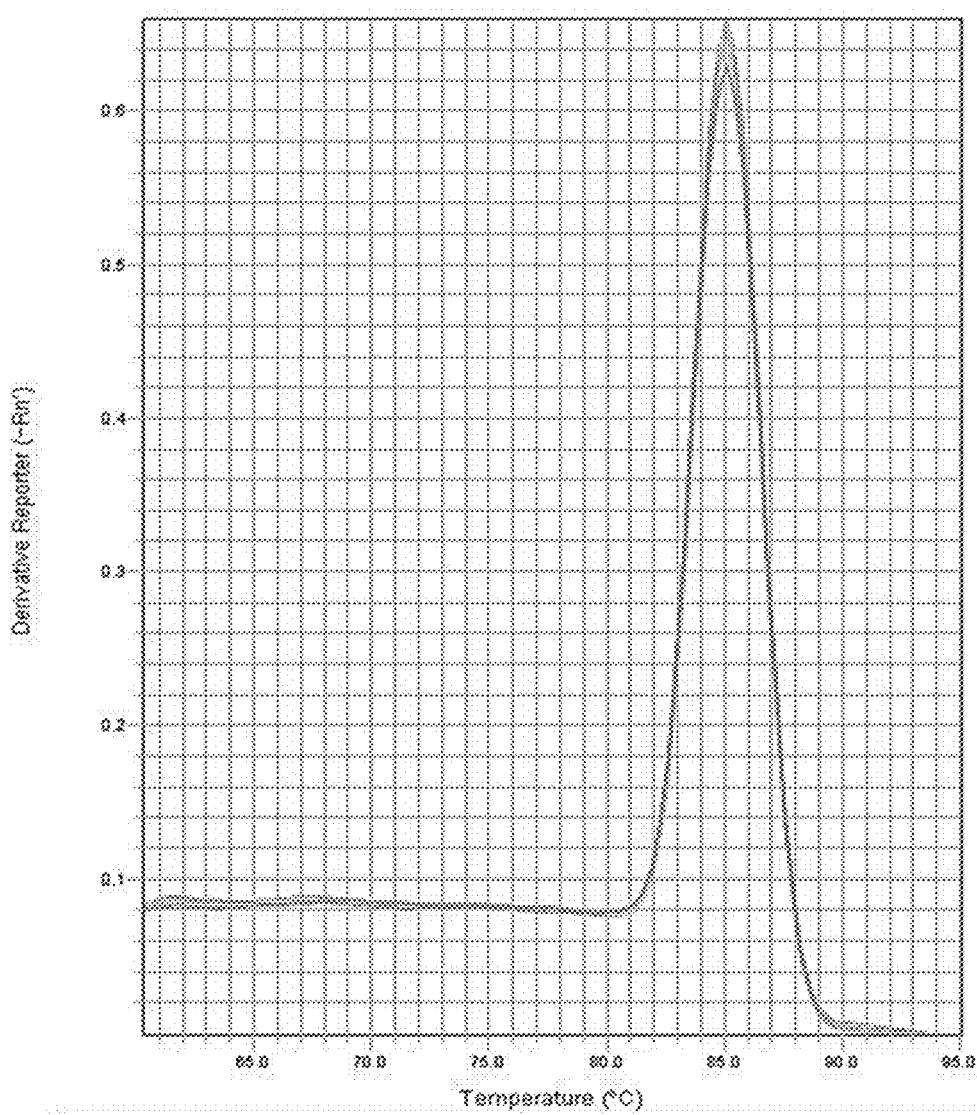
Figure 18-b
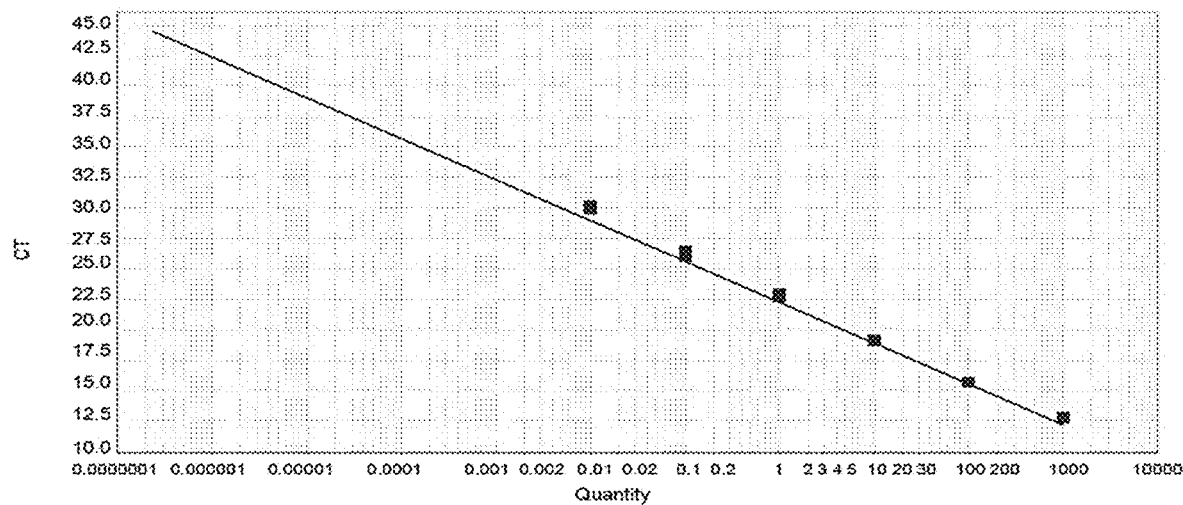
Figure 19-a

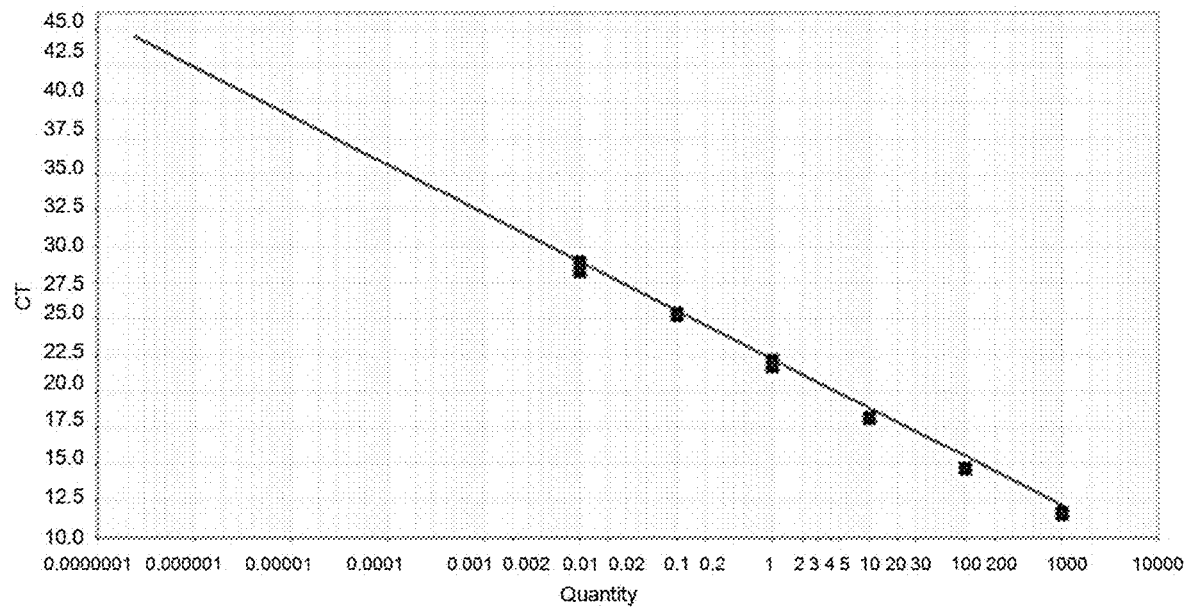
Figure 19-b
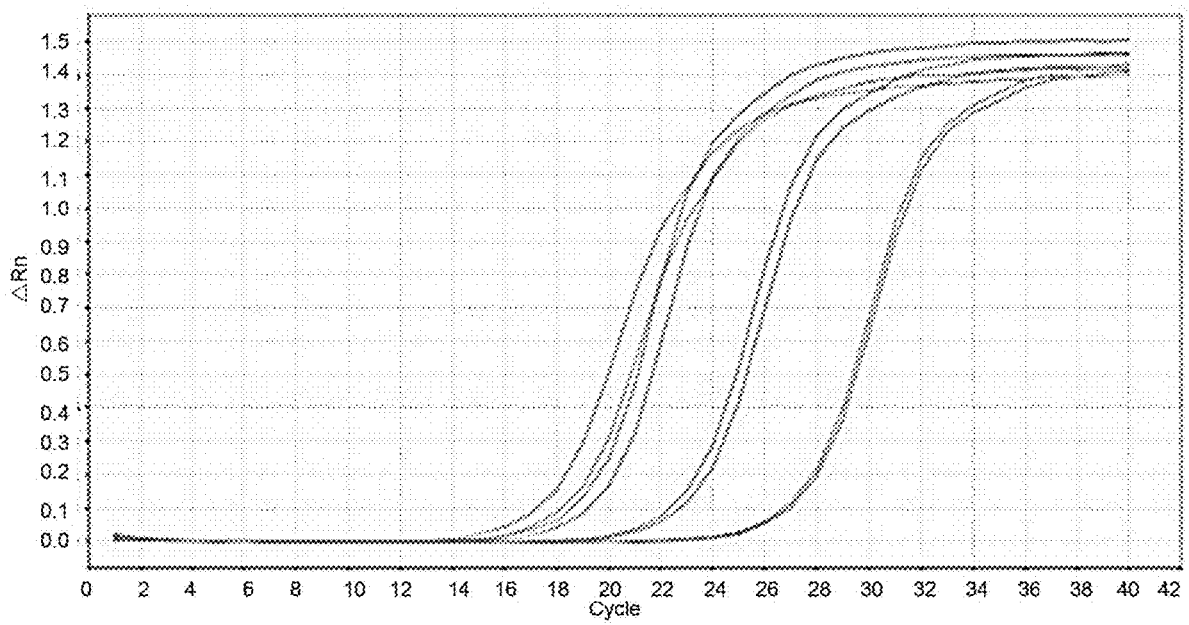
Figure 20-a

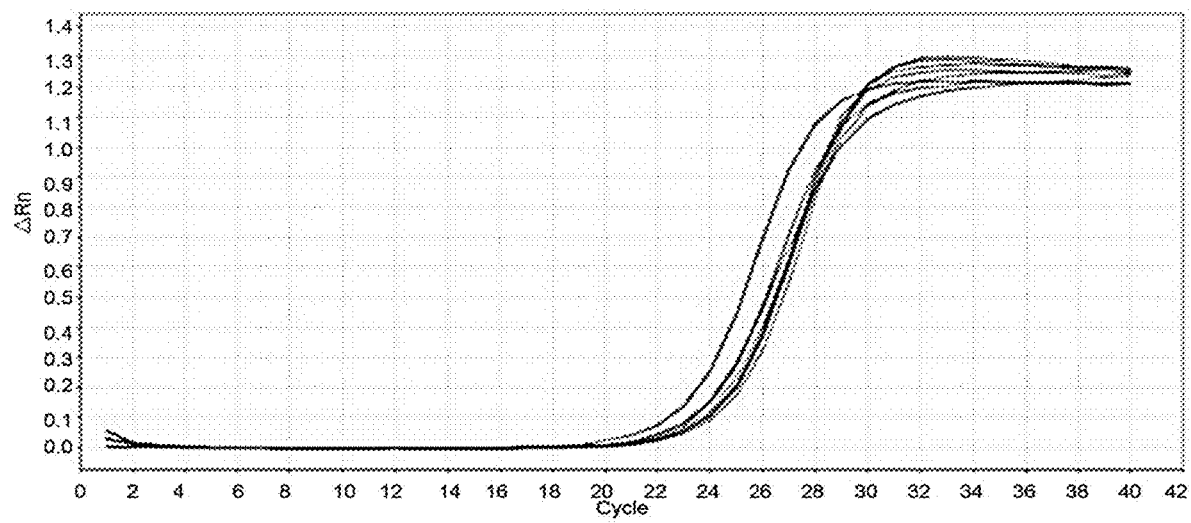
Figure 20-b
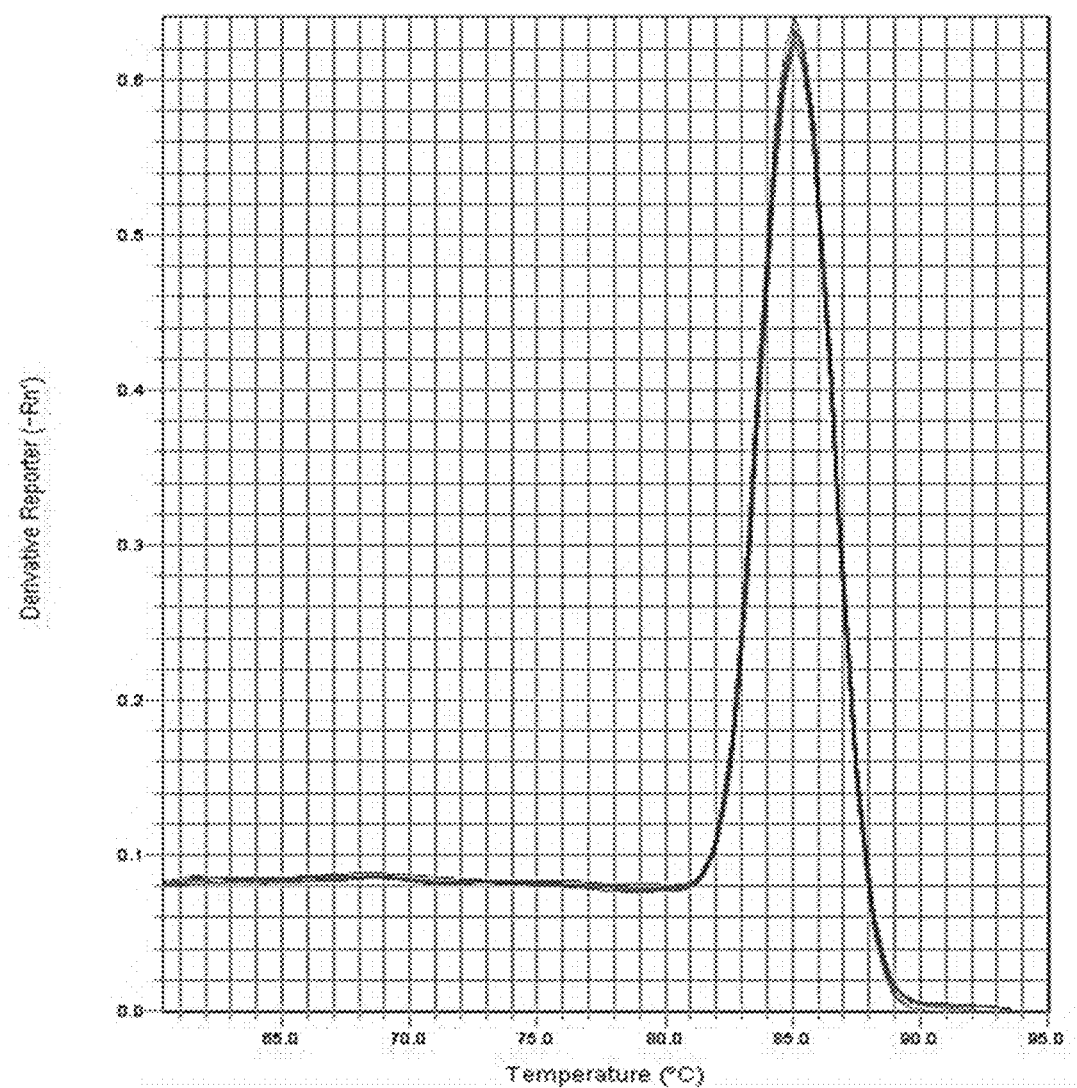
Figure 21-a

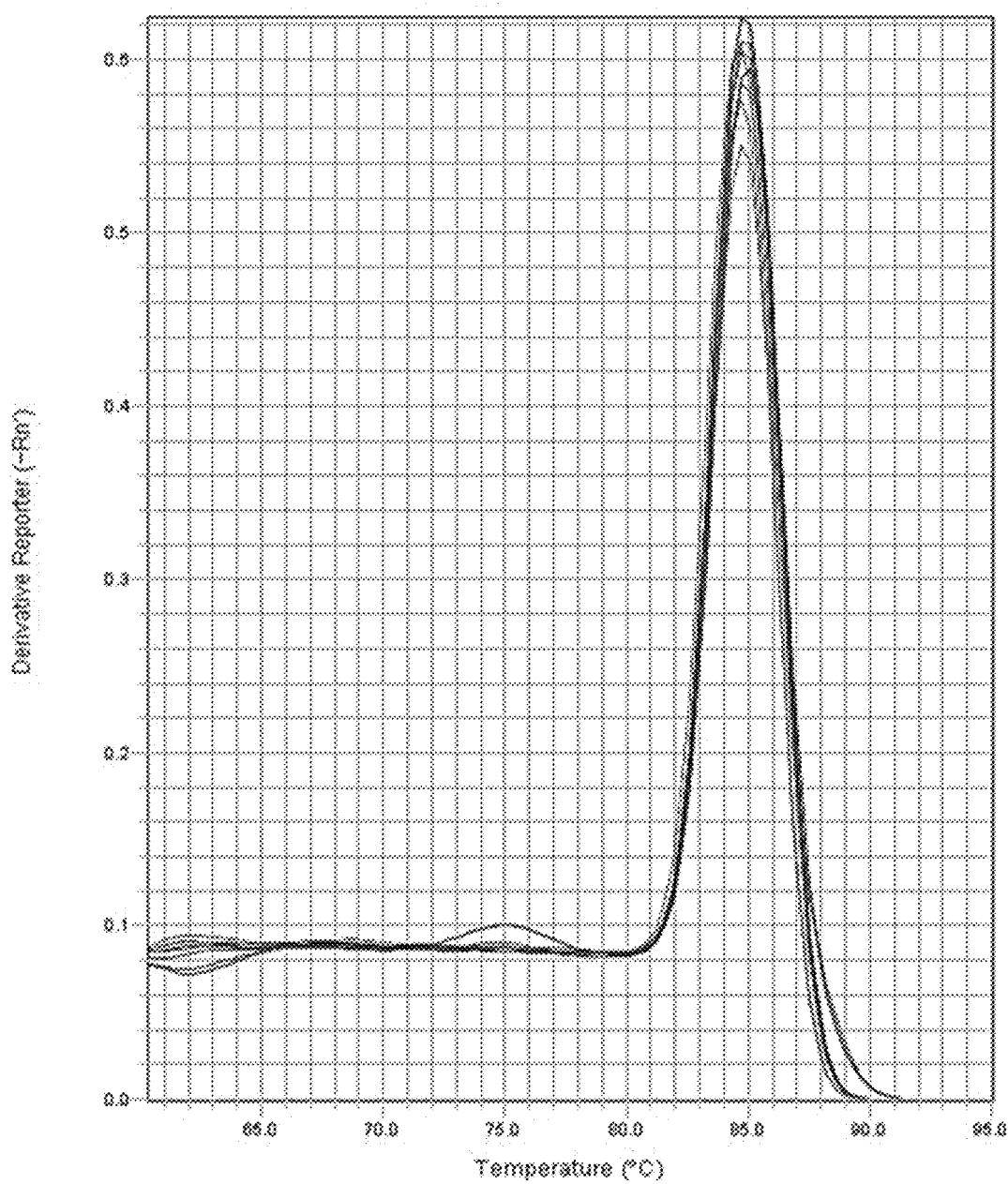
Figure 21-b

RECOMBINANT *DERMATOPHAGOIDES PTERONYSSINUS* TYPE 2 ALLERGEN PROTEIN AND ITS PREPARATION METHOD AND APPLICATION

SEQUENCE LISTING

The instant application contains a Sequence Listing which has been filed electronically in ASCII format and is hereby incorporated by reference in its entirety. Said ASCII copy, created on Nov. 25, 2019, is named 423-002US_SL.txt and is 5,388 bytes in size.

TECHNICAL FIELD

The invention belongs to the field of bioengineering genes, and relates to a recombinant *Dermatophagoides pteronyssinus* type 2 allergen, and its coding gene and expression and purification method.

BACKGROUND ART

There are many kinds of dust mites, which are widely present in human living and working environments. The excreta, metabolites and mite bodies of dust mites have strong allergenicity. According to statistics, about 10% of the world's population is allergic to dust mites, and about 80% of extrinsic asthma is caused by dust mites.

At present, a crude extract of dust mite allergens is mainly used clinically to treat allergic diseases caused by dust mites. Allergens of dust mites mainly exist in excreta and mite bodies; therefore, the extraction method takes a long time with a cumbersome process and a high cost. In addition, the composition of a natural allergen extract is very complicated, it is very difficult to make its components constant, and the natural allergen extract is easy to be contaminated by exogenous toxic substances and pathogenic microorganisms. Long-term use of a crude extract of dust mite allergens can lead to local reactions such as flush, swelling, induration and necrosis; and systemic reactions such as shock, edema, bronchospasm, urticaria, angioedema and systemic erythema. In addition, in the case that the crude extract is used for diagnosis, it is impossible to specifically determine the extent of the patient's response to each component of the allergens, which may lead to misdiagnosis.

The quality of the allergen is essential for the diagnosis and treatment of allergic diseases, and the allergen used for immunodiagnosis and immunotherapy should be a pure product rather than a crude extract. Recombinant allergens have the following advantages over crude extracts: (1) the recombinant allergens have a higher purity and contain no non-allergenic components, enzymes, enzyme inhibitors and toxic proteins as compared with the crude extracts; (2) the recombinant protein has a single composition, has good specificity, while the components in the crude extract are complex, the patient may only have reactions with some of the components of the crude extract, and the specificity is poor; (3) as compared with the natural extract, the recombinant allergen reduces IgE-bound antigenic epitopes and thus reduces IgE-mediated allergic reactions effectively, at the same time the domains of allergen necessary for T cell recognition are retained to result in better immunogenicity, thereby reducing the risk of immunotherapy and improving the desensitization therapy effect.

Allergens of dust mites are complex in composition, with more than 30 types, of which type 1 and type 2 allergens are the most important allergen components. In the serum of dust mite allergic patients, 70-80% of the patients had IgE binding to type 2 allergens, and showed strong positive reaction. The precursor of Der p2 was composed of 146 amino acids, and 129 amino acids remained after signal peptide removal. The molecular weight of Der p2 was 14 KD and there was no glycosylation site. At present, Stallergenes' patent in 2011 (European patent No. EP2388268 (A1)) is more representative of the research on Der p2 recombinant expression using eukaryotic expression system. They recombined and purified Der p2 using *Pichia pastoris* expression system. The patent did not optimize the Der p2 gene and molecule construction for *Pichia pastoris* system. It had low yield, complex purification process and was difficult to meet the clinical dosage.

SUMMARY OF THE INVENTION

In order to overcome the above-mentioned shortcomings, the inventors optimize the Der p2 gene in the *Pichia pastoris* expression system, and add an acting element to increase the expression of Der p2 in molecular level, and the inventors surprisingly find that Der p2 after gene optimization is expressed at a higher level as compared with the prior art, and has a similar biological activity as the natural protein.

One object of the present invention is to provide a DNA sequence encoding Der p2 protein, having a base sequence as shown in SEQ ID NO: 1. This sequence has been codon-optimized for the *Pichia pastoris* expression system, which is more conducive to expressing Der p2 in *Pichia pastoris*.

Another object of the present invention is to provide Der p2 protein having an amino acid sequence as shown in SEQ ID NO:3.

Another object of the present invention is to provide a vector comprising the above-mentioned optimized gene encoding Der p2, preferably, the vector is pAO815, pPIC9, pPIC9K, pPIC3.5, pPIC3.5K, pPICZ A, B, C or pGAPZ A, B, C, more preferably pPIC3.5K, pPICZ A or pGAPZ A.

Another object of the present invention is to provide a *Pichia pastoris* strain comprising the above-mentioned vector, preferably, the *Pichia pastoris* strain is SMD1168, GS115, KM71, X33 or KM71H, more preferably strain KM71 or X33.

Preferably, there is 242 bp interval between the DNA sequence encoding the Der p2 protein and the ATG of AOX1 of *Pichia pastoris*; the DNA sequence encoding the Der p2 protein is preceded by Kozak sequence GCCACCATGG (SEQ ID NO: 10).

Another object of the present invention is to provide a method for expressing the Der p2 protein, comprising the steps of:

A constructing a vector comprising the above-mentioned gene encoding Der p2;

B linearizing the vector of step A, transferring it into a *Pichia pastoris* strain, and culturing under a suitable condition;

C recovering and purifying the protein.

The above-mentioned vector is preferably pPIC3.5K, pPICZ A or pGAPZ A.

The above-mentioned *Pichia pastoris* strain is preferably a KM71 or X33 strain.

More preferably, the above-mentioned vector is pPICZ A, and the above-mentioned *Pichia pastoris* strain is strain X33.

Another object of the present invention is to provide a method for purifying a recombinant Der p2 protein, comprising the steps of:

A centrifuging the Der p2 fermentation broth at a low temperature and a high speed to collect a supernatant, ultrafiltering the supernatant against a 50 mM sodium acetate buffer at pH 4.0, and filtering through a 0.45 μm filter membrane;

B the first step, cation chromatography, comprising equilibrating a chromatographic column with an equilibration buffer, passing the Der p2 fermentation broth in step A through a separation packing using a purification system, and then eluting with a gradient of an elution buffer to collect an elution peak, wherein the equilibration buffer is 50 mM sodium acetate at pH 4.0, and the elution buffer is 50 mM sodium acetate and 1.0 M sodium chloride at pH 4.0;

C the second step, comprising ultra-filtrating the Der p2 protein peak collected in step B with a 20 mM phosphate solution at pH 6.0, equilibrating a chromatographic column with an equilibration buffer, loading the ultra-filtrated Der p2 protein solution on an anion chromatography packing, and collecting a flow-through peak, wherein the equilibration buffer is 20 mM phosphate at pH 6.0;

D the third step, comprising adding ammonium sulfate to the flow-through peak in step C to the final concentration of 1.5 M, pH 6.0, equilibrating a chromatographic column with an equilibration buffer, loading a Der p2 sample on a hydrophobic chromatography packing, eluting with a gradient of an elution buffer, wherein equilibration buffer is 1.5 M ammonium sulfate and 20 mM phosphate at pH 6.0, and the elution buffer is 20 mM phosphate at pH 6.0.

Another object of the present invention is to provide the use of the recombinant Der p2 protein in the preparation of a medicament for treating a dust mite allergic disease. The allergic disease is allergic rhinitis, allergic asthma, and the like.

The recombinant Der p2 protein of the present invention has a high expression level and has similar biological activity as the natural protein.

BRIEF DESCRIPTION OF THE DRAWINGS

FIG. 1 is a comparison plot of sequences of the recombinant Der p2 gene before and after optimization (SEQ ID NOS 2 and 1, respectively, in order of appearance).

The sequence before optimization corresponds to the nucleotide sequence of the natural Der p2 gene; the sequence after optimization corresponds to the nucleotide sequence of the recombinant Der p2 gene of the present invention, that is, the codon-optimized sequence.

FIGS. 2-*a* and 2-*b* show the CAI indices of the Der p2 gene in the *Pichia pastoris* expression system before and after optimization.

FIG. 2-*a* shows that the CAI index of the nucleotide sequence of the natural Der p2 gene in the *Pichia pastoris* expression system was calculated by a program to be 0.82. FIG. 2-*b* shows that the CAI index of the optimized Der p2 codon of the present invention in the *Pichia pastoris* expression system is calculated by a program to be 0.91.

FIGS. 3-*a* and 3-*b* are optimal codon frequency distribution region plots of the Der p2 gene in the *Pichia pastoris* expression host before and after codon optimization.

FIG. 3-*a* is an optimal codon frequency distribution region plot of the nucleotide sequence of natural Der p2 gene in the *Pichia pastoris* system, and it can be seen from the Figure that the occurrence percentage of low-utilization codon in the nucleotide sequence of natural Der p2 gene is 3%. FIG. 3-*b* shows an optimal codon frequency distribution region plot of the optimized Der p2 codon of the present invention in the *Pichia pastoris* system, and the occurrence rate of low-utilization codon in the sequence of optimized Der p2 codon of the present invention is 0.

FIGS. 4-*a* and 4-*b* are average GC base content distribution region plots of the Der p2 gene in the *Pichia pastoris* expression system before and after codon optimization.

FIG. 4-*a* shows that the average GC base content of the nucleotide sequence of the natural Der p2 gene in the *Pichia pastoris* expression system is 38.73%. FIG. 4-*b* shows that the average GC base content of optimized Der p2 codon of the present invention in the *Pichia pastoris* expression system is 45.96%.

FIG. 5 is an agarose gel electrophoretogram of a PCR product of the codon-optimized Der p2 gene.

Lane 1 represents 500 bp DNA ladder; lane 2 represents a PCR product of the recombinant Der p2 gene containing EcoRI and XhoI restriction sites at both ends.

FIG. 6 is a diagram showing a construction process of the expression plasmid pPICZ-Der p2 for codon-optimized Der p2.

FIG. 7 is a diagram showing the identification of expression of the codon-optimized Der p2 gene in the host engineering bacteria.

FIG. 7-*a* is a SDS-PAGE gel electrophoretogram of a supernatant of a solution of the host engineering strain containing the codon-optimized Der p2 gene, after methanol-induced expression for one week. Lane 1 represents pre-stained protein loading markers in the range of 10-250 KD; and lanes 2-9 represent supernatants of cultured solutions of Der p2 gene-positive monoclonal host engineering strains screened by Zeocin.

FIG. 7-*b* is a western blot plot of a supernatant of a solution of the host engineering strain containing the codon-optimized Der p2 gene, after methanol-induced expression for one week. Lane 1 represents pre-stained protein loading markers in the range of 10-250 KD; and lanes 2-9 represent supernatants of cultured solutions of Der p2 gene-positive monoclonal host engineering strains screened by Zeocin.

FIG. 8 shows a chromatogram of the supernatant of Der p2 fermentation broth by cation chromatography of the first step, and a gel electrophoretogram.

FIG. 8-*a* is a chromatogram of the supernatant of Der p2 fermentation broth by cation chromatography of the first step. FIG. 8-*b* is a gel electrophoretogram of samples collected by performing cation chromatography of the first step on the supernatant of Der p2 fermentation broth, wherein lane 3 represents 11-100 KD non-pre-stained protein markers, lane 1 represents the supernatant of the Der p2 fermentation broth before purification, lane 2 represents the flow-through liquid, and lanes 4-10 represent the elution of each tube.

FIG. 9 is a chromatogram of Der p2 protein by anion chromatography of the second step, and a gel electrophoretogram.

FIG. 9-*a* is a chromatogram of Der p2 protein by anion chromatography. FIG. 9-*b* is a gel electrophoretogram of samples collected by performing anion chromatography on Der p2 protein, wherein lane 4 represents 11-100 KD non-pre-stained protein markers, lane 1 represents the supernatant before purification of Der p2 protein, lane 2 represents the flow-through liquid of Der p2 protein, and lane 3-10 represent elution peaks of Der p2 protein.

FIG. 10 shows a chromatogram of Der p2 protein by hydrophobic chromatography of the third step and a gel electrophoretogram.

FIG. 10-a is a chromatogram of Der p2 protein by hydrophobic chromatography of the third step. FIG. 10-b is a gel electrophoretogram of samples collected by performing hydrophobic chromatography on Der p2 protein, wherein lane 1 represents 11-100 KD non-pre-stained protein markers, and lane 2-10 represent the elution of each tube FIG. 11 is the sequencing of N-terminal amino acids of Der p2 proteins.

FIG. 12 is an dot-immunoblot identification plot of recombinant Der p2 and natural Der p2 with positive serum respectively, wherein nDerp2 represents the natural Der p2 protein, rDerp2 represents the recombinant Der p2 protein, and NC represents a PBS solution at pH 7.4.

FIG. 13 is an agarose gel electrophoretogram of a PCR-amplified GAP gene, wherein lane 1 represents 250 bp DNA ladder and lane 2 represents the GAP gene.

FIG. 14 is an agarose gel electrophoretogram of positive clone of GAP gene T-vector identified by PCR, wherein lane 1 represents 250 bp DNA ladder, lanes 2-11 represent positive clones obtained by blue-white screening, and lane 12 represents a negative clone obtained by blue-white screening.

FIG. 15 is an agarose gel electrophoretogram of a PCR-amplified Der p2 gene, wherein lane 1 represents 500 bp DNA ladder and lane 2 represents the Der p2 gene.

FIG. 16 is an agarose gel electrophoretogram of for positive clone of Der p2 gene T-vector identified by PCR, wherein lane 2 represents 500 bp DNA ladder, lanes 1 and 3 represent negative clones obtained by blue-white screening, lanes 4-16 represent positive clones obtained by blue-white screening, and lane 17 represents a positive control (Der p2 gene).

FIG. 17 shows amplification curves of a standard plasmid.

FIG. 17-a shows amplification curves of the standard plasmid T-GAP, and FIG. 17-b shows amplification curves of the standard plasmid T-Der p2.

FIG. 18 shows melting curves of a standard plasmid.

FIG. 18-a shows melting curves of the standard plasmid T-GAP, and FIG. 18-b shows melting curves of the standard plasmid T-Der p2.

FIG. 19 shows a standard curve of a standard plasmid.

FIG. 19-a shows a standard curve of the standard plasmid T-GAP, and FIG. 19-b shows a standard curve of the standard plasmid T-Der p2.

FIG. 20 shows amplification curves of samples to be tested.

FIG. 20-a shows amplification curves obtained when the samples to be tested are amplified with GAP-1 and GAP-2 as primers, and FIG. 20-b shows amplification curves obtained when the samples to be tested are amplified with 5'AOX and 3'AOX as primers.

FIG. 21 shows melting curves of samples to be tested.

FIG. 21-a shows melting curves obtained when the samples to be tested are amplified with GAP-1 and GAP-2 as primers, and FIG. 21-b shows melting curves obtained when the samples to be tested are amplified with 5'AOX and 3'AOX as primers.

DETAILED DESCRIPTION OF EMBODIMENTS

The invention is further illustrated below in conjunction with specific examples. It should be understood that the examples referred to are merely illustrative of the invention and are not intended to limit the scope of the present invention.

Example 1 Codon Optimization of Recombinant Der p2

Based on the DNA sequence of Der p2 disclosed in GenBank (GenBank accession no. AAF86462), as shown in SEQ ID No: 2, the inventors performed codon optimization of the gene to obtain the Der p2 gene of the present invention of which the nucleotide sequence is as shown in SEQ ID No: 1 and the amino acid sequence is as shown in SEQ ID No: 3. Comparison of each parameter before and after codon optimization of the Der p2 is as follows:

1. Codon Adaptation Index (CAI)

As can be seen from FIG. 2-a, the codon adaptation index (CAI) of the original Der p2 gene in the *Pichia pastoris* expression system before codon optimization is 0.82. As can be seen from FIG. 2-b, the Der p2 gene has a CAI index of 0.91 in the *Pichia pastoris* expression system after codon optimization. Usually, when CAI=1, it is considered that the gene is in the most ideal expression state in the expression system. The lower the CAI index, the worse the expression level of the gene in the host. Thus, it can be seen the gene sequence obtained by codon optimization can increase the expression level of the Der p2 gene in the *Pichia pastoris* expression system.

2. Optimal Codon Usage Frequency (POP)

As can be seen from FIG. 3-a, based on the *Pichia pastoris* expression vector, the occurrence percentage of the low-utilization codon (codon with a utilization rate less than 40%) of the Der p2 gene sequence is 3% before codon optimization. This unoptimized gene uses tandem rare codons that may reduce translation efficiency and even disintegrate a translation assembly. As can be seen from FIG. 3-b, the Der p2 gene has a low utilization codon frequency of 0 in the *Pichia pastoris* system after codon optimization.

3. GC Base Content (GC Curve)

The ideal distribution region of GC content is 30%-70%, and any peak outside this region will affect transcription and translation efficiency to varying degrees. As can be seen from the comparison of the average GC base content distribution region plots of the Der p2 gene in FIG. 4-a and FIG. 4-b, FIG. 4-a shows the average GC base content of the Der p2 gene being 38.73%, and FIG. 4-b shows that the peaks of GC content appearing outside the 30%-70% region are removed after optimization, and finally the average GC base content of optimized Der p2 is 45.96%.

Example 2: Construction of an Expression Plasmid Containing the Der p2 Gene

A sequence of EcoRI restriction site was introduced at the 5' end, and a sequence of XhoI restriction site was introduced at the 3' end of the codon-optimized Der p2, and then full gene synthesis was performed. The synthesized gene fragment was constructed into the pUC57 plasmid supplied by GenScript (Nanjing) Co., Ltd., thereby obtaining a plasmid for long-term preservation, denoted as pUC57-Der p2 plasmid.

PCR amplification was performed using the pUC57-Der p2 plasmid as a template, and primers of following sequences:

```
upstream primer (SEQ ID No: 4):
M13 F:
TGT AAA ACG ACG GCC AGT downstream primer (SEQ ID No: 5):
M13 R:
CAG GAA ACA GCT ATG AC
```

The total volume of the reaction was 50 μL, in which 2.5 μL of each primer at a concentration of 10 μmol/L was added, 1 μL of dNTP at a concentration of 10 mmol/L was added, and 0.5 μL DNA polymerase being Q5 (#M0491L, purchased from New England BioLabs) at 2 U/μL was added. The reaction conditions were 98° C. for 5 seconds, 55° C. for 45 seconds, and 72° C. for 30 seconds. After 25 cycles, the product was analyzed by 1.0% agarose gel electrophoresis. The results showed that the product size was consistent with the expected size (500 bp) (results as shown in FIG. 5). The product was digested with EcoRI (#R0101S, purchased from New England BioLabs) and XhoI (#R0189S, purchased from New England BioLabs), respectively, and electrophoresed on 1% agarose gel to obtain a gene product, which was purified using a DNA gel recovery kit (DP214, purchased from Tiangen Biotech (Beijing) Co., Ltd.). The purified product was ligated to pPICZαA plasmid (V173-20, purchased from Invitrogen) with T4 ligase (#M0202S, purchased from New England BioLabs), and transformed into DH5a competent cells (CB101, purchased from Tiangen Biotech (Beijing) Co., Ltd.) and cultured in an LB solid medium containing bleomycin (purchased from Invitrogen) at 37° C. overnight. On the second day, the positive clones were picked and sequenced, and the sequence was found identical to the expected sequence by alignment, thereby obtaining the expression plasmid of codon-optimized Der p2, denoted as pPICZ-Der p2 (the plasmid construction was as shown in FIG. 6).

Example 3: Construction of a *Pichia pastoris* Host Engineering Strain Containing a Recombinant Der p2 Gene Formulation of YPDS solid medium: the medium was formulated according to the instructions of Easy SelectPichia Expression Kit, Invitrogen, comprising 10 g/L yeast extract, 20 g/L peptone, 20 g/L glucose, 15 g/L agarose, and 182 g/L sorbitol.

1. Construction of a Host Engineering Strain Containing Codon-Optimized Der p2

Electrocompetent cells were prepared according to the method of instructions of Easy SelectPichia Expression Kit, Invitrogen. The plasmid pPICZ-Der p2 obtained in Example 2 was linearized with Sac I restriction endonuclease (#R0156S, purchased from New England Biolabs), and precipitated with ethanol. The linearized vector was electrotransformed into competent cells of *Pichia pastoris* X33. The cells were plated on YPDS solid media and cultured at 30° C. until the transformants grew.

Example 4: Inducible Expression and Identification of Engineering Strains Containing Codon-Optimized Der p2 Gene Formulation of BMGY medium: the medium was formulated according to the instructions of Easy SelectPichia Expression Kit, Invitrogen, comprising 10 g/L yeast extract, 20 g/L peptone, 3 g/L $K_2HPO_4$, 11.8 g/L $KH_2PO_4$, 13.4 g/L YNB, $4\times10^{-4}$ g/L biotin, and 10 g/L glycerin.

Formulation of BMMY medium: the medium was formulated according to the instructions of Easy SelectPichia Expression Kit, Invitrogen, comprising 10 g/L yeast extract, 20 g/L peptone, 3 g/L $K_2HPO_4$, 11.8 g/L $KH_2PO_4$, 13.4 g/L YNB, $4\times10^{-4}$ g/L biotin, and 5 mL/L methanol.

1. Methanol-Induced Expression of an Engineering Strain of Codon-Optimized Der p2

The host monoclonal engineering strain obtained in Example 3 was picked into a 5 mL BMGY medium and cultured in a 50 mL sterile centrifuge tube at 30° C. and 220 rpm until $OD_{600}$ reaches 1.0-2.0. 1 mL of the culture was stored, and the remaining strain solution was resuspended and transferred to BMMY for induced expression at a small scale, and methanol was supplemented every 24 hours to a final concentration of 1%. One week later, the supernatant of the strain solution was collected by centrifugation, and analyzed by SDS-PAGE gel electrophoresis and Western blotting. Brightness of expressed product bands was observed. FIGS. 7-*a* and 7-*b* are plots of identification of induced expression of gene engineering strains containing Der p2. As seen from FIGS. 7-*a* and 7-*b*, the Der p2 protein was significantly expressed in the engineering strain.

Example 5: Purification of Recombinant Der p2 Protein

The Der p2 constructed in this invention is obtained mainly by ion exchange and hydrophobic chromatography purification methods. HiTrap SP FF, HiTrap Q FF, and HiTrap Phenyl HP were selected as the chromatographic packings. The specific steps are as follows:

1. Pretreatment of the Fermentation Broth by Impurity Removal

The fermentation broth of host engineering strain containing Der p2 obtained according to Example 4 was centrifuged at a low temperature at 12000 rpm for 15 minutes to collect a supernatant, and the supernatant was ultrafiltered against a 50 mM sodium acetate buffer at pH 4.0 for 48 h, and filtered through a 0.45 μm filter membrane to obtain a supernatant of the treated fermentation broth.

2. Cation Exchange Chromatography

The treated fermentation broth of the previous step was loaded on a SPFP cation exchange chromatographic column, wherein the equilibration buffer was 50 mM NaAc at pH 4.0, the elution buffer was 50 mM NaAc and 1.0 M NaCl at pH 4.0, isocratic elution was performed at 12%, 25% and 100%, and the sample peaks were mainly concentrated at the 25% elution peak. FIG. 8-*a* is an ion exchange purification chromatogram of Der p2, and FIG. 8-*b* is an SDS-PAGE analysis plot of Der p2 after ion exchange chromatography.

3. Anion Exchange Chromatography

The Der p2 protein peak purified in the previous step was collected, and the sample was ultrafiltered with a 20 mM Tris-HCl solution at pH 8.0, and loaded on a HiTrap Q FF chromatography packing. The equilibration buffer was 20 mM Tris-HCl at pH 8.0, and the elution buffer was 20 mM Tris-HCl and 1.0 M NaCl at pH 8.0. Equivalent elution was carried out according to 25%, 50% and 100%. Der p2 protein is mainly concentrated in the penetration peak. FIG. 9-*a* is Der p2 anion exchange purification chromatogram, and FIG. 9-*b* is SDS-PAGE identification map of Der p2 after anion exchange chromatography.

4. Hydrophobic Chromatography

The flow-through peak of Der p2 from the anion chromatography was collected, and ammonium sulfate was added to a final concentration of 1.5 M. The fermentation broth supernatant treated as above was loaded on a Phenyl HP chromatographic column. The equilibration buffer was 20 mM $NaH_2PO_4$ and 1.5 M $(NH_4)_2SO_4$ at pH 6.0; the elution buffer was 20 mM $NaH_2PO_4$ at pH 6.0, isocratic elution was performed at 25%, 50%, 70%, and 100%, and the Der p2 protein is mainly concentrated at the 75% elution peak. FIG. 10-a is hydrophobic chromatography purification chromatogram of Der p2, and FIG. 10-b is an SDS-PAGE analysis plot of Der p2 after hydrophobic chromatography. The yield of target protein per liter of fermentation broth is as high as 200 mg or more.

Example 6: Sequence Analysis of N-Terminal Amino Acids of Protein

The determination of N-terminal sequence of proteins and polypeptides is one of the important links in the quality control of pharmaceutical industry. In this experiment, N-terminal sequence analysis based on classical Edman degradation method was used.

The N-terminal sequence of Der p2 protein purified from Example 5 was analyzed by Shimadzu Automatic Protein Peptide Sequencing Instrument (PPSQ-33A, SHIMADZU). The results showed in FIG. 11 that the first five amino acids of N-terminal were DQVDV (SEQ ID NO: 10), which indicated that the N-terminal five amino acid sequences of the recombinant Der p2 protein constructed and expressed were identical to those of the natural protein.

Example 7: Analysis of Der p2 Protein Activity

The purified Der p2 protein was dialyzed against a PBS buffer at pH 7.4, and the protein concentration was determined by a BCA protein concentration assay kit (Cat No: 23225, purchased from Pierce), and fold-diluted to 250 ng, 125 ng, 62.5 ng, 31.25 ng, and 15.625 ng. Using the dot immunoblotting method, the obtained solution was detected for the reactivity with sera of patients allergic to *Dermatophagoides pteronyssinus* by comparing with natural Der p2 as the control. FIG. 12 shows a dot immunoblot plot of recombinant Der p2 and natural Der p2 (NA-DP2-1, purchased from Indoor Biotechnologies) with positive serum, and the results indicate that the recombinant Der p2 has substantially identical reactivity with the sera as compared with the natural Der p2, showing that the recombinant Der p2 has a similar biological activity as the natural Der p2.

Example 8: Determination of Gene Copy Number of Recombinant Der p2 Engineering Strain 1. Inoculation X33 strain: the strains were cultured in YPD media for 24 h, the X33 genome was extracted by a genomic extraction kit (purchased from Tiangen Biotech (Beijing) Co., Ltd.), and GAP gene was amplified using the X33 genome as a template, and GAP-1 and GAP-2 as primers of which the sequences are as follows:

```
upstream primer (SEQ ID No: 6)
GAP-1:
GGTATTAACGGTTTCGGACGTATTG
```

```
downstream primer (SEQ ID No: 7)
GAP-2:
GATGTTGACAGGGTCTCTCTCTTGG
```

The total volume of the reaction was 50 µL, in which 2.5 µL of each primer at a concentration of 10 µmol/L was added, 1 µL of dNTP at a concentration of 10 mmol/L was added, and 0.5 µL DNA polymerase being Taq DNA Polymerase (M0267S, purchased from New England BioLabs) at 2 U/µL was added. The reaction conditions were 94° C. for 10 minutes, 94° C. for 30 seconds, 55° C. for 30 seconds, 68° C. for 30 seconds, and 68° C. for 5 minutes. After 30 cycles, the product was analyzed by 1.0% agarose gel electrophoresis. The results showed that the product size was consistent with the expected size (400 bp) (results as shown in FIG. 13). The obtained gene product was purified by DNA gel recovery kit (DP214, purchased from Tiangen Biotech (Beijing) Co., Ltd.) and ligated into pGM-T vector kit (VT202-01, purchased from Tiangen Biotech (Beijing) Co., Ltd.). The Top10 competent cells (CB104, purchased from Tiangen Biotech (Beijing) Co., Ltd.) were transformed with the vector, and cultured at 37° C. overnight on blue-white screening media. On the next day, white clones were picked and identified by PCR for which the primers used were GAP-1 and GAP-2. The PCR reaction conditions were consistent with the above-mentioned conditions. The obtained product was analyzed by 1.0% agarose gel electrophoresis, and the results showed that the product size is consistent with the expected size (400 bp) (results as shown in FIG. 14). The positive clones were sent to GenScript (Nanjing) Co., Ltd. for sequencing, and the sequence was found completely identical to the expected sequence by alignment, thereby obtaining the T vector clone of GAP gene, denoted as T-GAP. The T-GAP clone having a correct sequence was inoculated in an LB liquid medium at 37° C. overnight, and the plasmid was extracted (using a plasmid mini-extract kit DP103, purchased from Tiangen Biotech (Beijing) Co., Ltd.) to obtain a standard plasmid for real-time quantitative PCR.

2. The Der p2 gene was amplified using the pPICZα-Der p2 plasmid of Example 2 as a template, and 5' AOX and 3' AOX as primers with the following sequences:

```
upstream primer (SEQ ID No: 8):
5'AOX:
GACTGGTTCCAATTGACAAGC
```

```
downstream primer (SEQ ID No: 9):
3'AOX:
GGCAAATGGCATTCTGACAT
```

The total volume of the reaction was 50 µL, in which 2.5 µL of each primer at a concentration of 10 µmol/L was added, 1 µL of dNTP at a concentration of 10 mmol/L was added, and 0.5 µL DNA polymerase being Taq DNA Polymerase (#M0267S, purchased from New England BioLabs) at 2 U/µL was added. The reaction conditions were 94° C. for 10 minutes, 94° C. for 30 seconds, 49° C. for 30 seconds, and 68° C. for 60 seconds, and 68° C. for 5 minutes. After 30 cycles, the product was analyzed by 1.0% agarose gel electrophoresis. The results showed that the product size was consistent with the expected size (750 bp) (results as shown in FIG. 15). The obtained gene product was purified by DNA gel recovery kit (DP214, purchased from Tiangen Biotech (Beijing) Co., Ltd.) and ligated into pGM-T vector kit (VT202-01, purchased from Tiangen Biotech (Beijing) Co., Ltd.). The Top10 competent cells (CB104, purchased from Tiangen Biotech (Beijing) Co., Ltd.) were transformed with the vector, and cultured at 37° C. overnight on blue-white screening media. On the next day, white clones were picked and identified by PCR for which the primers used were 5'AOX and 3'AOX. The PCR reaction conditions were consistent with the above-mentioned conditions. The obtained product was analyzed by 1.0% agarose gel electrophoresis, and the results showed that the product size is consistent with the expected size (750 bp) (results as shown in FIG. 16). The positive clones were sent to GenScript (Nanjing) Co., Ltd. for sequencing, and the sequence was found completely identical to the expected sequence by alignment, thereby obtaining the T vector clone of Der p2, denoted as T-Der p2. The T-Der p2 clone having a correct sequence was inoculated in an LB liquid medium at 37° C. overnight, and the plasmid was extracted using a plasmid mini-extract kit (DP103, purchased from Tiangen Biotech (Beijing) Co., Ltd.) to obtain a standard plasmid for real-time quantitative PCR.

3. Calculation of gene copy number:

The concentration (ng/μL) of the standard plasmid was determined by a nucleic acid microanalyzer (Nanodrop2000, ThermoFisher). Copy numbers of GAP and Der p2 were calculated according to the following formula:

$$\text{Copies}/u = (6.02 \times 10^{23}) 3 \text{ pies } \mu L \times 3p^{-9})/(\text{DNA length} 02 \times 10$$

4. Processing samples to be tested

The pPICZ-Der p2-X33 engineering strain was inoculated in YPD liquid media at 30° C. overnight; and the genome was extracted the next day, and its concentration (ng/μL) and purity were determined by a nucleic acid quantitative microanalyzer.

5. Establishment of a standard curve

The standard plasmids of T-GAP and T-Der p2 with known copy numbers were gradiently diluted to $10^8$, $10^7$, $10^6$, $10^5$, $10^4$, and $10^3$ copies/μl, respectively. The fluorescent quantitative PCR were performed using GAP-1 and GAP-2, 5' AOX and 3' AOX as primers, respectively. FIG. 17-a shows amplification curves of the standard plasmid T-GAP, FIG. 17-b shows amplification curves of the standard plasmid T-Der p2, FIG. 18-a shows melting curves of the standard plasmid T-GAP, and FIG. 18-b shows melting curves of the standard plasmid T-Der p2. Each gradient was assayed 3 times to verify the repeatability of the standard curve. Standard curves were established with the Ct values as the ordinate and the starting template copy numbers as the abscissa. FIG. 19-a shows a standard curve of the standard plasmid T-GAP, and FIG. 19-b shows a standard curve of the standard plasmid T-Der p2.

6. Determination of Copy Number of Der p2 Gene in Recombinant Strains

The genome sample of extracted pPICZ-Der p2-X33 was serially 10-fold-diluted to obtain four gradients of stock solution, $10^{-1}$, $10^{-2}$, and $10^{-3}$. Fluorescent quantitative PCR was performed using GAP-1 and GAP-2, 5' AOX and 3' AOX as primers, and each gradient was assayed three times. FIG. 20-a shows amplification curves of the samples to be tested with GAP-1 and GAP-2 as primers, FIG. 20-b shows amplification curves of the samples to be tested with 5' AOX and 3' AOX as primers, FIG. 21-a shows melting curves of the samples to be tested with GAP-1 and GAP-2 as primers, and FIG. 21-b shows melting curves of the samples to be tested with 5' AOX and 3' AOX as primers. The GAP gene exists in Pichia pastoris in a single copy. Therefore, the copy number of the GAP gene can be used to characterize the initial copy number of the genome in the template. The ratio of the copy number of the Der p2 gene to the copy number of the GAP gene is the copy number of Der p2 gene in the Pichia pastoris genome. Table 1 shows the detection results of copy number of the Der p2 gene in the Pichia pastoris gene engineering strain, the detected copy number is between 5.75 and 6.26, and finally the copy number of the Der p2 gene in the recombinant strain was averaged to eliminate the system error and determined to be 6.

TABLE 1

Results of copy number of Der p2 in the genome detected by real-time fluorescent quantitative PCR

| DNA concentration | GAP gene | Der p2 gene | GAP gene | Der p2 gene | Copy number of the Der p2 gene/copy number of the GAP gene |
|---|---|---|---|---|---|
| Stock solution | 19.06 | 23.52 | 6.52 | 5.77 | 6.26 |
| $10^{-1}$ | 22.87 | 24.02 | 5.81 | 5.76 | 6.03 |
| $10^{-2}$ | 27.50 | 24.45 | 4.10 | 5.48 | 5.87 |
| $10^{-3}$ | 29.76 | 24.59 | 3.62 | 5.39 | 5.75 |

(Average Ct value gene copy number ($10^N$) Copy number of Der p2 gene in Pichia pastoris genome)

Example 9: Analysis of the Acting Elements in the Der p2 Genome

There is no stable additional plasmid in Pichia pastoris, the expression vector is homologously recombined with the host chromosome, and the exogenous gene expression framework is fully integrated into the chromosome to realize the expression of the exogenous gene; the typical Pichia pastoris expression vector contains a regulatory sequence of alcohol oxidase gene, and contains the main structures comprising AOX promoter, multiple cloning site, transcription termination and polyA formation gene sequence (TT), screening markers and the like. The promoter is a cis-element for gene expression regulation and an important element for the genetically engineered expression vector. The important role of the promoter at the transcriptional level determines the gene expression level.

The Der p2 genome was extracted according to the method of Example 8, and the Der p2 gene was amplified from the genome using 5' AOX and 3' AOX as primers according to the method in Step 2 of Example 8. The obtained samples were sent to GenScript (Nanjing) Co., Ltd. to detect the acting element before and after the Der p2 gene which was inserted into the genome. The results of genome sequencing indicated that the Der p2 gene expression framework was integrated into the chromosome of Pichia pastoris by a single cross-insertion, which enabled the Der p2 gene to express the gene using the AOX promoter on the yeast chromosome, and thus the expression level was higher.

Generally, the closer the first ATG of the exogenous coding sequence to the ATG of AOX1, the better the expression effect. In the gene construction, the inventors chose an enzyme cleavage site closest to the ATG of AOX1, and found that the Der p2 gene was away from ATG of AOX1 only by 242 bp. In addition, Kozak sequence GCCACCATGG (SEQ ID NO: 10) was added in front of Der p2 gene, and the signal peptide and the sequence can greatly improve transcription and translation efficiency and increase expression efficiency of Der p2 gene in eukaryotes.

The invention claimed is:

1. A DNA encoding a Der p2 protein, having a base sequence as shown in SEQ ID NO: 1.

2. A vector comprising the DNA of claim 1, wherein the vector is pAO815, pPIC9, pPIC9K, pPIC3.5, pPIC3.5K, pPICZα A, B, C or pGAPZ A, B, C.

3. A host cell comprising the vector of claim 2, wherein the host cell is a cell of *Pichia pastoris* strain SMD1168, GS115, KM71, X33 or KM71H.

4. The vector of claim 2, wherein there is a 242 bp interval between the base sequence encoding the Der p2 protein and ATG of AOX1 of *Pichia pastoris*; and the base sequence encoding the Der p2 protein is preceded by Kozak sequence GCCACCATGG (SEQ ID NO: 10).

* * * * *

SEQUENCE LISTING

<160> NUMBER OF SEQ ID NOS: 11

<210> SEQ ID NO 1
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgatgtaca agatcttgtg tttgtctttg ttggttgctg ctgttgctag agaccaggtt      60
gacgttaagg actgtgctaa ccacgagatc aagaaggttt tggttccagg ttgtcacggt     120
tccgagccat gtattattca cagaggtaag ccattccagt tggaggctgt tttcgaagct     180
aaccagaaca ctaagactgc taagattgag atcaaggctt ccatcgacgg tttggaagtt     240
gacgttccag gtattgaccc aaacgcttgt cactacatga agtgtccatt ggttaagggt     300
cagcagtacg acatcaagta cacttggaat gttccaaaga tcgctccaaa gtccgagaac     360
gttgttgtta ctgttaaggt tatgggtgac gacggtgttt tggcttgtgc tattgctact     420
cacgctaaga tcagagacta a                                               441
```

<210> SEQ ID NO 2
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgatgtaca aaattttgtg tctttcattg ttggtcgcag ccgttgctcg tgatcaagtc      60
gatgtcaaag attgtgccaa tcatgaaatc aaaaaagttt tggtaccagg atgccatggt     120
tcagaaccat gtatcattca tcgtggtaaa ccattccaat tggaagccgt tttcgaagcc     180
aaccaaaaca caaaaacggc taaaattgaa atcaaagcct caatcgatgg tttagaagtt     240
gatgttcccg gtatcgatcc aaatgcatgc cattacatga atgcccatt ggttaaagga     300 caacaatatg atattaaata tacatggaat gttccgaaaa ttgcaccaaa atctgaaaat     360
gttgtcgtca ctgttaaagt tatgggtgat gatggtgttt tggcctgtgc tattgctact     420
catgctaaaa tccgcgatta a                                               441
```

<210> SEQ ID NO 3
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Met Tyr Lys Ile Leu Cys Leu Ser Leu Leu Val Ala Ala Val Ala
1               5                   10                  15

Arg Asp Gln Val Asp Val Lys Asp Cys Ala Asn His Glu Ile Lys Lys
            20                  25                  30

Val Leu Val Pro Gly Cys His Gly Ser Glu Pro Cys Ile Ile His Arg
        35                  40                  45

Gly Lys Pro Phe Gln Leu Glu Ala Val Phe Glu Ala Asn Gln Asn Thr
    50                  55                  60
```

-continued

```
Lys Thr Ala Lys Ile Glu Ile Lys Ala Ser Ile Asp Gly Leu Glu Val
 65                  70                  75                  80

Asp Val Pro Gly Ile Asp Pro Asn Ala Cys His Tyr Met Lys Cys Pro
                 85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Val Thr Val Lys Val Met
        115                 120                 125

Gly Asp Asp Gly Val Leu Ala Cys Ala Ile Ala Thr His Ala Lys Ile
    130                 135                 140

Arg Asp
145

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtaaaacga cggccagt                                                 18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caggaaacag ctatgac                                                  17

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtattaacg gtttcggacg tattg                                         25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatgttgaca gggtctctct cttgg                                         25

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 8
gactggttcc aattgacaag c                                              21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcaaatggc attctgacat                                                20

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Gln Val Asp Val
1               5

<210> SEQ ID NO 11
<211> LENGTH: 10
<212> TYPE: DNA
<213> ORGANISM: Unknown
<220> FEATURE:
<223> OTHER INFORMATION: Description of Unknown:
      Kozak sequence

<400> SEQUENCE: 11
gccaccatgg                                                           10
```